United States Patent [19]

Kazmaier et al.

[11] Patent Number: 4,746,756

[45] **Date of Patent: * May 24, 1988**

[54] PHOTOCONDUCTIVE IMAGING MEMBERS WITH NOVEL FLUORINATED SQUARAINE COMPOUNDS

[75] Inventors: Peter M. Kazmaier; Giuseppa Baranyi, both of Mississauga; Rafik O. Loutfy, Willowdale, all of Canada

[73] Assignee: Xerox Corporation, Stamford, Conn.

[ * ] Notice: The portion of the term of this patent subsequent to Jun. 4, 2002 has been disclaimed.

[21] Appl. No.: 899,197

[22] Filed: Aug. 21, 1986

Related U.S. Application Data

[62] Division of Ser. No. 748,285, Jun. 24, 1985, Pat. No. 4,621,038.

[51] Int. Cl.[4] .......... C07C 85/00; C07C 85/02; C07C 85/06

[52] U.S. Cl. .......... 564/307; 546/94; 546/304; 546/329; 546/334; 546/346; 548/400; 548/469; 548/483; 548/557; 548/558

[58] Field of Search .......... 564/307; 548/400, 469, 548/483, 557, 558; 546/94, 304, 329, 334, 346

[56] References Cited

U.S. PATENT DOCUMENTS

| | | | |
|---|---|---|---|
| 2,957,918 | 10/1960 | Smutny et al. | 260/590 |
| 3,617,270 | 11/1971 | Kampler | 96/1.7 |
| 4,028,418 | 6/1977 | van den Brink et al. | 260/586 C |
| 4,052,209 | 10/1977 | Huffman et al. | 96/1.5 R |
| 4,159,387 | 6/1979 | Bellus | 560/185 |
| 4,216,172 | 8/1980 | Heine et al. | 568/364 |
| 4,222,902 | 9/1980 | Hoffman et al. | 252/500 |
| 4,346,157 | 8/1982 | Kakuta et al. | 430/58 |
| 4,391,889 | 7/1983 | Mabuchi et al. | 430/59 |
| 4,396,694 | 8/1983 | Nagata et al. | 430/58 |
| 4,420,548 | 12/1983 | Salai et al. | 430/59 |
| 4,471,041 | 9/1984 | Baranyi et al. | 430/59 |
| 4,481,270 | 11/1984 | Kubota et al. | 430/55 |
| 4,486,520 | 12/1984 | Yanus | 430/59 |
| 4,489,148 | 12/1984 | Horgan | 430/59 |
| 4,490,452 | 12/1984 | Champ et al. | 430/58 |
| 4,500,621 | 2/1985 | Wurster | 430/72 |
| 4,507,480 | 3/1985 | Horgan et al. | 546/94 |
| 4,508,803 | 4/1985 | Lau et al. | 430/59 |
| 4,508,811 | 4/1985 | Gravesteijn et al. | 430/270 |
| 4,521,621 | 6/1985 | Yanus et al. | 564/307 |
| 4,523,035 | 6/1985 | Yanus | 564/307 |
| 4,524,218 | 6/1985 | Baranyi et al. | 564/307 |
| 4,524,219 | 6/1985 | Law | 564/307 |
| 4,524,220 | 6/1985 | Law | 564/307 |
| 4,525,592 | 6/1985 | Law et al. | 564/307 |
| 4,552,822 | 11/1985 | Kazmaier et al. | 564/307 X |
| 4,585,895 | 4/1986 | Law | 564/307 |
| 4,624,904 | 11/1986 | Kazmaier et al. | 564/307 X |
| 4,626,485 | 12/1986 | Kin et al. | 564/307 X |

OTHER PUBLICATIONS

"The Chemistry of Squaraines," Schmidt, Arthur H., Oxocarbon (1980), pp. 185–231, Edited by Robert West, Academic: New York Press.

*Primary Examiner*—Paul F. Shaver
*Attorney, Agent, or Firm*—E. O. Palazzo

[57] ABSTRACT

Disclosed are fluorinated squaraine compounds of the following formula:

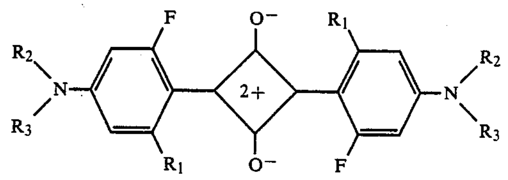

wherein $R_1$, $R_2$ and $R_3$ are independently selected from the group consisting of alkyl, aryl, and heterocyclic substituents.

7 Claims, 2 Drawing Sheets

PHOTOCONDUCTIVE IMAGING MEMBERS WITH NOVEL FLUORINATED SQUARAINE COMPOUNDS

This is a division of application Ser. No. 748,285, filed June 24, 1985, now U.S. Pat. No. 4,621,038.

BACKGROUND OF THE INVENTION

This invention is generally directed to novel squaraine compositions of matter, and the incorporation thereof into layered photoresponsive imaging members. More specifically, the present invention relate to layered photoresponsive imaging members having incorporated therein as photogenerating pigments specific novel fluorinated squaraine compounds. In one embodiment, the photoresponsive imaging member of the present invention is comprised of a photoconductive layer containing the novel fluorinated squaraine compounds illustrated herein, and an aryl amine hole transport layer. Also encompassed within the present invention are imaging members which are responsive to visible light, and infrared illumination needed for laser printing, which members can comprise, in addition to a hole transport layer, a photogenerating layer, and a photoconductive layer containing the novel fluorinated squaraine compounds illustrated herein. Accordingly, the aforementioned imaging members can function so as to enhance or reduce the intrinsic properties of a charge carrier photogenerating material contained therein in the infrared and/or visible range of the spectrum thereby allowing the member to be sensitive to either visible light and/or infrared wavelengths. Further, imaging members without the photogenerating layer are sensitive to either visible light, and/or infrared wavelengths.

Numerous different xerographic photoconductive members are known including, for example, a homogeneous layer of a single material such as vitreous selenium, or a composite layered device with a dispersion of a photoconductive composition. An example of one type of composite xerographic photoconductive member is described in U.S. Pat. No. 3,121,006 wherein there is disclosed finely divided particles of a photoconductive inorganic compound dispersed in an electrically insulating organic resin binder. These members comprise coated on a paper backing a binder layer containing particles of zinc oxide uniformly dispersed therein. The binder materials disclosed in this patent include polycarbonate resins, polyester resins, and polyamide resins, which resins are incapable of transporting for any significant distance injected charge carriers generated by the photoconductive particles. Accordingly, as a result the photoconductive particles must be in a substantially contiguous particle to particle contact throughout the layer for the purpose of permitting charge dissipation required for a cyclic operation.

There are also known photoreceptor members comprised of inorganic or organic substances wherein the charge carrier generating, and charge carrier transport functions are accomplished by discrete contiguous layers. Additionally, layered photoreceptor devices are disclosed in the prior art which include an overcoating of an electrically insulating polymeric material. However, the art of xerography continues to advance and there is desired other layered photoresponsive devices which are responsive to visible light, and/or infrared illumination.

Recently, there has been disclosed layered photoresponsive devices comprised of separate generating layers, and transport layers, reference U.S. Pat. No. 4,265,990; and overcoated photoresponsive materials with a hole injecting layer, reference U.S. Pat. No. 4,251,612. Examples of photogenerating layers disclosed in these patents are trigonal selenium, and phthalocyanines, while examples of transport layer molecules include the aryl amine diamines as mentioned herein. The disclosures of each of the aforementioned U.S. Pat. Nos. 4,265,990 and 4,251,612 are totally incorporated herein by reference.

Many other patents are in existence that describe layered photoresponsive devices with generating pigments, such as U.S. Pat. No. 3,041,167, which discloses an overcoated imaging member containing a conductive substrate, a photoconductive layer, and an overcoating layer of an electrically insulating polymeric material. This member is utilized in an electrophotographic copying method by, for example, initially charging the layered device with an electrostatic charge of a first polarity, and imagewise exposing to form an electrostatic latent image which can be subsequently developed. Prior to each succeeding imaging cycle, the imaging member can be charged with an electrostatic charge of a second opposite polarity. Sufficient additional charges of the second polarity are applied so as to create across the member a net electrical field of the second polarity. Simultaneously, mobile charges of the first polarity are created in the photoconductive layer by applying an electrical potential to the conductive substrate. The imaging potential which is developed is present across the photoconductive layer and the overcoating layer.

There is also disclosed in Belgian Pat. No. 763,540 an electrophotographic member having at least two electrically operative layers. One of these layers is comprised of a photoconductive substance which is capable of photogenerating charge carriers, and injecting the carriers into a continuous active layer containing an organic transporting material which is substantially non-absorbing in the spectral region of intended use. Additionally, there is disclosed in U.S. Pat. No. 3,041,116 a photoconductive device containing a transparent plastic material overcoated on a layer of vitreous selenium present on a substrate.

Furthermore, there is disclosed in U.S. Pat. Nos. 4,232,102 and 4,233,383, photoresponsive imaging members comprised of trigonal selenium doped with sodium carbonate, sodium selenite, and trigonal selenium doped with barium carbonate, and barium selenite or mixtures thereof. Moreover, there is disclosed in U.S. Pat. No. 3,824,099 certain photosensitive hydroxy squaraine compositions. According to the disclosure of this patent, the squaraine compositions are photosensitive in normal electrostatographic imaging systems.

Also, there is disclosed in U.S. Pat. No. 4,415,639 the use of hydroxy squaraines as a photoconductive compound in an infrared sensitive photoresponsive device. More specifically, there is described in this patent an improved photoresponsive device with a substrate, a hole blocking layer, an optional adhesive interfacial layer, an inorganic photogenerating layer, a photoconductive composition capable of enhancing or reducing the intrinsic properties of the photogenerating layer, which photoconductive composition is selected from various squaraine compositions, including hydroxy squaraine compositions, and a hole transport layer.

Additionally, there is illustrated in U.S. Pat. No. 4,471,041, the disclosure of which is totally incorporated herein by reference, the use of novel julolidinyl squaraine compositions, such as bis-9-(8-hydroxyjulolidinyl)squaraine, as photoconductive substances in photoresponsive devices which are sensitive either to infrared light, and/or visible illumination. It is indicated in this patent that the improved photoresponsive device in one embodiment is comprised of a supporting substrate, a hole blocking layer, an optional adhesive interfacial layer, an inorganic photogenerating layer, a photoconducting composition capable of enhancing or reducing the intrinsic properties of the photogenerating layer, which composition is comprised of the novel julolidinyl squaraine compositions disclosed therein, and a hole transport layer.

There is further disclosed in U.S. Pat. No. 4,486,520, the disclosure of which is totally incorporated herein by reference, photoresponsive imaging members with photogenerating layers of certain novel fluorinated squaraine compositions. Examples of specific fluorinated squaraines disclosed include bis(4-dimethylamine-2-fluorophenyl) squaraine, bis(4-[N,N,diethylamino-2-fluorophenyl] squaraine, bis(4-[N-methyl-N-ethyl-2-fluoroanilinel) squaraine, bis(4-[N,N-dibenzyl-2-fluoroaniline]) squaraine, bis(4-[N-methyl-N-benzyl-2-fluoroaniline]) squaraine, bis(4-[N-ethyl-N-benzyl-2-fluoroaniline]) squarine, and the like. Other useful fluorinated squaraine compositions include bis[4-[N,N,-di(4-chlorophenylmethyl)-2-fluorophenyl]) squaraine, bis(4-[N-methyl-N-(4-chlorophenylmethyl)-2-fluorophenyl]) squaraine, and bis(4-[N-benzyl-N-(-chlorophenylmethyl)-2-fluorophenyl]) squaraine. While the squaraines of the present invention are similar to those as disclosed in the aforementioned patent, they differ in a number of significant respects, particularly for example the squaraine compounds of the present invention have present on each of the benzene rings attached to the squaric acid moiety, in addition to fluorine atoms at specific positions, various organic groups as disclosed herein. Moreover, the fluorinated squaraine compounds of the present invention are of superior xerographic performance in comparison to those as described in U.S. Pat. No. 4,486,520. The squaraine compounds of the present invention also possess, in many instances, different spectral response, dark decay properties, and physical characteristics, inclusive of solubility parameters, than those squaraines of the above patent.

Therefore, while numerous squaraine compositions are known, there continues to be a need for novel squaraine compositions, particularly squaraine compositions of superior photosensitivity. Additionally, there continues to be a need for photoresponsive imaging members containing as a photoconductive layer highly sensitive fluorinated squaraine compositions of matter. Further, there continues to be a need for novel fluorinated squaraine compounds which when selected for layered photoresponsive imaging members allow for the generation of acceptable images, which members can also be repeatedly used in a number of imaging cycles without deterioration thereof from the machine environment or surrounding conditions. Moreover, there continues to be a need for improved layered imaging members with certain fluorinated photogenerating pigments which are substantially inert to the users of such members. Furthermore, there continues to be a need for overcoated photoresponsive imaging members which are sensitive to a broad range of wavelengths; and more specifically, are sensitive to infrared light and visible light thereby permitting their use in a number of imaging and printing systems. There is also a need for new specific fluorinated squaraine photogenerating pigments which simultaneously possess high photosensitivity, low dark decay properties, and high charge acceptance values.

SUMMARY OF THE INVENTION

It is therefore an object of the present invention to provide novel fluorinated squaraine compositions of matter useful for incorporation into photoconductive imaging members.

In another object of the present invention there are provided specific novel fluorinated squaraine compounds for incorporation into improved photoconductive imaging members, which members are panchromatic, and thus sensitive to visible light as well as infrared light.

A further specific object of the present invention is the provision of an improved overcoated photoresponsive imaging member containing therein a photoconductive layer comprised of specific fluorinated squaraine photosensitive pigments, and an aryl amine hole transport layer.

It is yet another object of the present invention to provide photoresponsive imaging members containing therein an aryl amine hole transport layer, and coated thereover a photoconductive layer comprised of specific fluorinated squaraine compounds.

In yet another object of the present invention there are provided photoresponsive imaging members with a photoconductive layer comprised of the fluorinated squaraine compositions illustrated herein situated between a hole transport layer, and a photogenerating layer.

It is yet another object of the present invention to provide an improved layered overcoated photoresponsive imaging member containing as a photoconductive layer the fluorinated squaraine compounds illustrated herein situated between a photogenerating layer and a supporting substrate.

Another object of the present invention resides in the provision of an improved photoresponsive imaging members with a photogenerating composition situated between an aryl amine hole transport layer, and a photoconductive layer comprised of the novel fluorinated squaraine compounds described herein, which members are simultaneously responsive to infrared light and visible light.

In yet still another object of the present invention there is provided improved overcoated photoresponsive imaging members containing a photoconductive layer comprised of specific fluorinated squaraine compounds described herein situated between an aryl amine hole transport layer, and a layer comprised of a photogenerating composition, which members are simultaneously responsive to infrared light and visible light.

Additionally, another object of the present invention resides in the provision of imaging and printing methods with the photoresponsive imaging members described herein.

In yet a further object of the present invention there are provided processes for obtaining in high yields specific novel fluorinated squaraine compounds.

Also, in a further object of the present invention there are provided novel fluorinated squaraine compounds which simultaneously possess high photosensitivity, low dark decay properties, and superior charge acceptance values; and are sensitive to visible and infrared wavelengths.

These and other objects of the present invention are accomplished by providing certain novel fluorinated squaraine compositions of matter of the following formula:

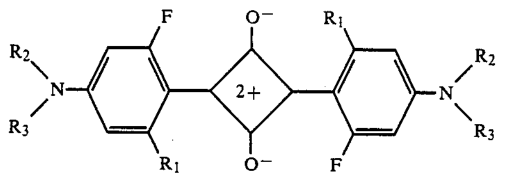

wherein $R_1$, $R_2$ and $R_3$ are independently selected from alkyl, aryl, and heterocyclic substituents. Illustrative examples of alkyl groups include those of from about 1 to about 20 carbon atoms such as methyl, ethyl, propyl, butyl, pentyl, hexyl, octyl, nonyl, decyl, pentadecyl and the like, with methyl, ethyl, propyl and butyl being preferred. In one specific preferred embodiment of the present invention, the alkyl groups are methyl.

Aryl substituents are those of from about 6 to about 24 carbon atoms, such as phenyl, naphthyl, anthryl and the like, with phenyl being preferred. Heterocyclic substituent examples are 2-pyrolyl, 3-indolyl, 4-pyridyl, and other similar groups.

Illustrative specific examples of novel fluorinated squaraine compounds included within the scope of the present invention are bis(4-dimethylamino-2-fluoro-6-methylphenyl) squaraine, bis(4-dimethylamino-6-ethyl-2-fluorophenyl) squaraine, bis(6-butyl-4-dimethylamino-2-fluorophenyl) squaraine, bis(4-dimethylamino-2-fluoro-6-phenylphenyl) squaraine, bis(4-ethylmethylamino-2-fluoro-6-methylphenyl) squaraine, bis(2-fluoro-4-methyl[phenylmethyl]amino-6-methylphenyl) squaraine, bis(4-[4'-chlorophenylmethyl]methylamino-2-fluoro-6-methylphenyl) squaraine, bis(4-[2'-(3',5'-dimethyl)pyrryl]methylamino-2-fluoro-6-methylphenyl) squaraine, bis(2-fluoro-4-[3'-(1'-methyl-)indolyl]methylamino-6-methylphenyl) squaraine, and bis(2-fluoro-4-methyl[4'-pyridyl]amino-6-methylphenyl) squaraine.

The specific novel squaraine compounds disclosed herein are generally prepared by the reaction of equal molar quantities of an aromatic fluorinated amine and squaric acid in the presence of an aliphatic alcohol, and an optional azeotropic cosolvent. Alternatively, an excess of amine, from about 2 equivalents to about 8 equivalents, can be selected for the reaction. About 400 milliliters of alcohol per 0.1 moles of squaric acid are selected, however, up to 1,000 milliliters of alcohol to 0.1 moles of squaric acid can be used. Additionally, from about zero to about 1,000 milliliters of azeotropic solvent are selected for this process. Further, the aforementioned reaction is usually accomplished at a temperature of from about 75° C. to about 130° C., and preferably at a temperature of 95° to 105° C., with stirring until the reaction is completed. Subsequently, the desired product is isolated from the reaction mixture by known techniques such as filtration, and the product resulting is identified by analytical tools including NMR, and mass spectroscopy. Moreover carbon, hydrogen, fluorine, nitrogen, and oxygen elemental analysis is selected for aiding in the identification of the resultant product.

Aromatic fluorinated amine reactants selected for the process illustrated herein include those of the following formula:

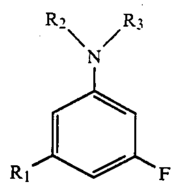

wherein $R_1$, $R_2$ and $R_3$ are as defined hereinbefore. Specific examples of fluorinated amine reactants are 1-dimethylamino-3-fluoro-5-methylbenzene, 1-dimethylamino-5-ethyl-3-fluorobenzene, 5-butyl-1-dimethylamino-3-fluorobenzene, 1-dimethylamino-3-fluoro-5-phenylbenzene, 1-ethylmethylamino-3-fluoro-5-methylbenzene, 3-fluoro-1-methyl(phenylmethyl)amino-5-methylbenzene, 1-[4'-chlorophenylmethyl]methylamino-3-fluoro-5-methylbenzene, 1-[2'-(3',5'-dimethyl)pyrryl]methylamino-3-fluoro-5-methylbenzene, 3-fluoro-1-(3'-[1'-methyl]indoly)methylamino-5-methylbenzene, and 3-fluoro-1-methyl(4'-pyridyl)amino-5-methylbenzene. These amines can be prepared by the known reaction of a fluoroaniline with a trialkyl phosphate as illustrated hereinafter.

Illustrative examples of aliphatic alcohols selected for preparing the novel fluorinated squaraines of the present invention include 1-butanol, 1-pentanol, hexanol, heptanol, 2-ethylhexanol and mixtures thereof; while illustrative examples of azeotropic materials that can be selected are aromatic compositions such as benzene, toluene, xylene, trichlorobenzene, and quinoline.

The fluorinated squaraine compounds of the present invention may also be prepared by the reaction of a dialkyl squarate, and an appropriate aromatic fluorinated aniline, in the presence of a catalyst and an aliphatic alcohol, as described in copending application U.S. Ser. No. 557,796 entitled Process for Squaraine Compositions, the disclosure of which is totally incorporated herein by reference. More specifically, this process embodiment comprises reacting at a temperature of from about 60° C. to about 160° C., a dialkyl squarate with a dialkyl aromatic fluorinated amine in the presence of an acid catalyst, and an aliphatic alcohol. Illustrative examples of dialkyl squarate reactants disclosed in the copending application include dimethyl squarate, dipropyl squarate, diethyl squarate, dibutyl squarate, dipentyl squarate, dihexyl squarate, diheptyl squarate, dioctyl squarate, and the like, with the dimethyl, diethyl, dipropyl and dibutyl squarates being preferred. Examples of fluoroaniline reactants include N,N-dimethylfluoroaniline, N,N-diethylfluoroaniline, N,N-dipropylfluoroaniline, N,N-dibutylfluoroaniline, N,N-dipentylfluoroaniline, N,N-dihexylfluoroaniline, 3-methyl-N,N-dimethylfluoroaniline, 3-hydroxy-N,N-dimethylfluoroaniline, 3-fluoro-N,N-dimethylfluoroaniline, 3-hydroxy-N,N-diethylfluoroaniline, 3-ethyl-N,N-dimethylfluoroaniline, and the like.

The improved layered photoresponsive imaging members of the present invention are comprised in one embodiment of a supporting substrate, a hole transport layer, and as a photogenerating or photoconductive layer situated therebetween one of the novel fluorinated squaraine compounds of the present invention. In another embodiment, there is envisioned a layered photoresponsive device comprised of a supporting substrate, a photoconductive layer comprised of one of the novel fluorinated squaraine compositions of the present invention, and situated therebetween a hole transport layer Also, provided in accordance with the present invention are improved photoresponsive devices useful in printing systems comprising a layer of a fluorinated squaraine photoconductive composition situated between an optional photogenerating layer and a hole transport layer; or wherein the fluorinated squaraine photoconductive composition is situated between a photogenerating layer and the supporting substrate of such a device. In the latter devices, the photoconductive layer serves to enhance, or reduce the intrinsic properties of the photogenerating layer in the infrared and/or visible range of the spectrum.

In one specific illustrative embodiment, the improved photoresponsive device of the present invention is comprised of (1) a supporting substrate; (2) a hole blocking layer; (3) an optional adhesive interface layer, and/or a layer of N-methyl-3-aminopropyl-trimethoxy silane; (4) an inorganic photogenerator layer; (5) a photoconducting composition layer capable of enhancing or reducing the intrinsic properties of the photogenerating layer, which composition is comprised of the novel squaraine materials described herein; and (6) a hole transport layer. Thus, the photoresponsive device of the present invention in one important embodiment can be comprised of a conductive supporting substrate, a hole blocking metal oxide layer in contact therewith, an adhesive layer, an inorganic photogenerating material overcoated on the adhesive layer, a fluorinated squaraine photoconducting composition capable of enhancing or reducing the intrinsic properties of the photogenerating layer in the infrared and/or visible range of the spectrum, and an aryl diamine hole transport layer. The photoconductive layer composition when in contact with the hole transport layer permits the movement of holes, and also the photoconductive squaraine composition layer can function as a selective filter allowing light of a certain wavelength to penetrate the photogenerating layer.

In another important embodiment, the present invention is directed to an improved photoresponsive device as described hereinbefore, with the exception that the photoconductive composition capable of enhancing or reducing the intrinsic properties of the photogenerating layer is situated between the photogenerating layer and the supporting substrate present in the device. Accordingly, in this variation, the photoresponsive device of the present invention is comprised of (1) a substrate; (2) a hole blocking layer; (3) an optional adhesive or adhesion interface layer; (4) a photoconductive composition capable of enhancing or reducing the intrinsic properties of a photogenerating layer in the infrared and/or visible range of the spectrum, which composition is comprised of the novel squaraine compounds disclosed herein; (5) an inorganic photogenerating layer; and (6) a hole transport layer.

Exposure to illumination and erasure of the layered photoresponsive devices of the present invention may be accomplished from the front side, the rear side, or combinations thereof.

The improved photoresponsive devices of the present invention can be prepared by a number of known methods, the process parameters and the order of coating of the layers being dependent on the device desired. Thus, for example, a three layered photoresponsive device can be prepared by a vacuum sublimation of the photoconducting layer on a supporting substrate, and subsequently depositing by solution coating the hole transport layer. In another process variant, the layered photoresponsive device can be prepared by providing the conductive substrate containing a hole blocking layer and an optional adhesive layer; and applying thereto by solvent coating processes, laminating processes, or other methods, a photogenerating layer, a photoconductive composition comprised of the novel squaraines of the present invention, which squaraines are capable of enhancing or reducing the intrinsic properties of the photogenerating layer in the infrared and/or visible range of the spectrum, and a hole transport layer.

In one specific preparation sequence, there is provided a 20 percent transmissive aluminized Mylar substrate of a thickness of about 75 microns, followed by coating with a 12.5 micron Bird applicator of an adhesive, such as the adhesive available for E. I. DuPont as polyester 49,000, in a trichloroethylene/trichloroethane solvent. Subsequently, there is applied to the adhesive layer with a Bird applicator a photoconductive layer comprised of a fluorinated squaraine of the present invention with annealing at 135° C., followed by the coating of an amine transport layer. The amine transport layer is applied by known solution coating techniques, with a 125 micron Bird applicator, and annealing at 135° C. wherein the solution is comprised of about 50 percent by weight of the amine transport molecule, and 50 percent by weight of a resinous binder such as a polycarbonate material.

The improved photoresponsive devices of the present invention can be incorporated into various imaging systems, like those conventionally known as xerographic imaging processes. Additionally, the photoresponsive devices of the present invention with an inorganic photogenerating layer, and a photoconductive layer comprised of the novel squaraines of the present invention can function simultaneously in imaging and printing systems with visible light and/or infrared light. In this embodiment, the photoresponsive members of the present invention may be negatively charged, exposed to light in a wavelight of from about 400 to about 1,000 nanometers, either sequentially or simultaneously, followed by developing the resulting image and transferring to paper.

BRIEF DESCRIPTION OF THE DRAWINGS

For a better understanding of the present invention and further features thereof reference to made to the following detailed description of various preferred embodiments wherein.

DESCRIPTION OF THE PREFERRED EMBODIMENTS

The preferred embodiments will now be illustrated with reference to specific photoresponsive imaging members with the novel fluorinated squaraine compositions illustrated herein, it being understood that equivalent compositions are also embraced within the scope of the present invention.

Figure 1:
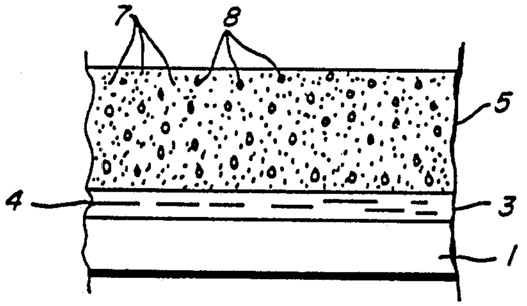
FIG. 1 is a partially schematic cross-sectional view of the photoresponsive imaging of the present invention.

Illustrated in FIG. 1 is a photoresponsive imaging member of the present invention comprised of a substrate 1, a photoconductive layer 3 comprised of a novel fluorinated squaraine composition illustrated herein, optionally dispersed in a resinous binder composition 4, and a charge carrier hole transport layer 5 comprised of charge transporting molecules 7 dispersed in an inactive resinous binder composition 8.

Figure 2:
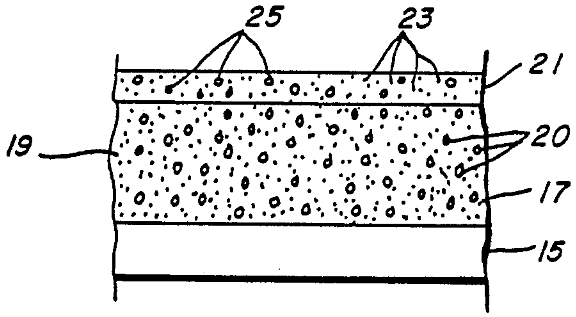
FIG. 2 is a partially schematic cross-sectional view of a further photoresponsive imaging member of the present invention.

Illustrated in FIG. 2 is essentially the same imaging member as illustrated in FIG. 1 with the exception that the hole transport layer is situated between the supporting substrate and the photoconductive layer. More specifically, with reference to FIG. 2 there is illustrated a photoresponsive imaging member comprised of a supporting substrate 15, a hole transport layer 17, comprised of aryl amine hole transporting molecules 19 dispersed in an inert resinous binder composition 20, and a photoconductive layer 21 comprised of a fluorinated squaraine compound of the present invention 23, optionally dispersed in a resinous binder composition 25.

Figure 3:
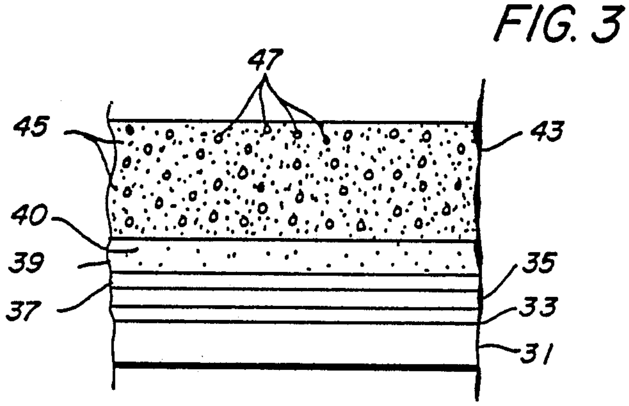
FIGS. 3 and 4 are partially schematic cross-sectional views of additional photoresponsive imaging members embraced by the present invention.

Illustrated in FIG. 3 is an improved photoresponsive imaging member of the present invention comprised of a substrate 31; a hole blocking metal oxide layer 33; an optional adhesive layer 35; and/or as an additional hole blocking layer a silane, reference U.S. Pat. No. 4,464,450, the disclosure of which is totally incorporated herein by reference; a charge carrier inorganic photogenerating squaraine composition 40; and capable of enhancing or reducing the intrinsic properties of the photogenerating layer 37 in the infrared and/or visible range of the spectrum; and a charge carrier or hole transport layer 43 comprised of aryl amine hole transporting molecules 45 dispersed in an inactive resinous binder 47.

Figure 4:
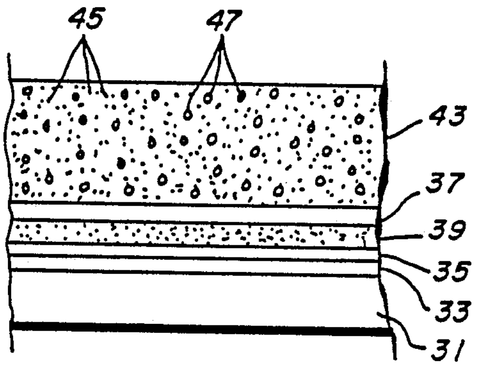

Illustrated in FIG. 4 is essentially the same imaging member as illustrated in FIG. 3 with the exception that the photoconductive layer 39 is situated between the inorganic photogenerating layer 37 and the supporting substrate 31. More specifically, the photoconductive layer in this embodiment, reference FIG. 4, is located between the optional adhesive layer 35 and the inorganic photogenerating layer 37.

Figure 5:
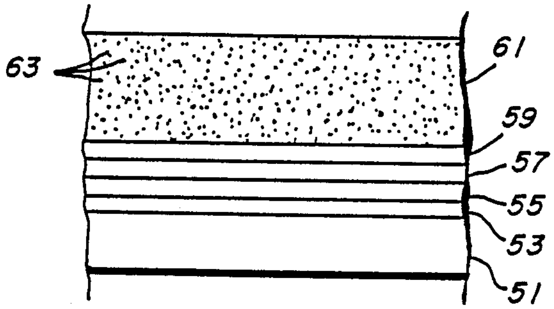
FIG. 5 is a partially schematic cross-sectional view of a photoresponsive imaging member of the present invention.

Illustrated in FIG. 5 is a photoresponsive imaging member of the present invention wherein the substrate 51 is comprised of Mylar in a thickness of 75 microns containing a layer of 20 percent transmissive aluminum in a thickness of about 100 Angstroms; a metal oxide layer 53 comprised of aluminum oxide in a thickness of about 20 Angstroms; a polyester adhesive layer 55, commercially available from E. I. DuPont as 49,000 polyester, in a thickness of 0.5 microns, an inorganic photogenerating layer 57 of a thickness of about 2.0 microns and comprised of 10 volume percent of $Na_2SeO_3$ and $Na_2CO_3$ doped trigonal selenium dispersed in a polyvinylcarbazole binder, 90 volume percent; a photoconductive layer 59 in a thickness of about 0.5 microns, and comprised of 30 volume percent of a fluorinated squaraine dispersed in the resinous binder Formvar ®, commercially available from Monsanto Chemical Company, 70 volume percent; and a hole transport layer 61 in a thickness of about 25 microns, comprised of 50 weight percent of N,N'-diphenyl-N,N'-bis(3-methylphenyl)-[1,1'-biphenyl]-4,4'-diamine dispersed in a polycarbonate resinous binder 63, 50 percent by weight.

With further reference to the Figures, the substrate layers may be opaque or substantially transparent, and can comprise any suitable material having the requisite mechanical properties. Thus, the substrate may comprise a layer of insulating material such as an inorganic or organic polymeric material, including Mylar a commercially available polymer; a layer of an organic or inorganic material with a semiconductive surface layer such as indium tin oxide, or aluminum arranged thereon, or a conductive material like, for example, aluminum, chromium, nickel brass or the like. The substrate can be flexible or rigid and many have a number of many different configurations, including for example a plate, a cylindrical drum, a scroll, an endless flexible belt, and the like. Preferably, the substrate is in the form of an endless flexible belt. In some situations, it may be desirable to coat on the back of the substrate, particularly when the substrate is an organic polymeric material, an anticurl layer, such as for example polycarbonate materials commercially available as Makrolon.

The thickness of the substrate layer depends on many factors, including economical considerations, thus this layer may be of substantial thickness, for example, over 2,500 microns, or of minimum thickness, providing the objectives of the present invention are attained. In one preferred embodiment, the thickness of this layer is from about 75 microns to about 250 microns.

With regard to the hole blocking metal oxide layers, they can be comprised of various suitable known materials including aluminum oxide and the like. The preferred metal oxide layer is aluminum oxide. The primary purpose of this layer is to provide hole blocking, that is, to prevent hole injection from the substrate during and after charging. Typically, this layer is of a thickness of less than 50 Angstroms.

The inorganic photogenerating layer can be comprised of known photoconductive charge carrier generating materials sensitive to visible light, such as amorphous selenium, amorphous selenium alloys, halogen doped amorphous selenium, halogen doped amorphous selenium alloys, trigonal selenium, mixtures of Groups IA and IIA elements, selenite and carbonates with trigonal selenium, reference U.S Pat. Nos. 4,232,102 and 4,223,283, the disclosure of each of these patents being totally incorporated herein by reference; cadmium sulfide, caldmium sulfur telluride, cadmium telluride, cadmium sulfur selenide, cadmium sulfur telluride, cadmium seleno telluride, copper, and chlorine doped cadmium sulfide; cadmium selenide; cadmium sulfur selenide, and the like. Alloys of selenium include selenium tellurium alloys, selenium arsenic alloys, selenium tellurium arsenic alloys, and preferably such alloys with a halogen material such as chlorine in an amount of from about 50 to about 200 parts per million.

Also, the photogenerating layer can have present therein organic materials including, for example, metal phthalocyanines, metal-free phthalocyanines, vanadyl phthalocyanines and the like. Examples of many of these phthalocyanine compounds are disclosed in U.S. Pat. No. 4,265,990, the disclosure of which is totally incorporated herein by reference. Preferred organic compounds for the photogenerating layer are vanadyl phthalocyanine and x-metal-free phthalocyanine. This layer typically is of a thickness of from about 0.05 microns to about 10 microns or more, and preferably is of a thickness from about 0.4 microns to about 3 microns;

however, the width of this layer is primarily dependent on the photoconductive volume loading, which may vary from 5 to 100 volume percent. Generally, it is desirable to provide the photogenerating layer in a thickness sufficient to absorb about 90 percent or more of the incident radiation which is directed thereupon in the imagewise, or printing exposure step. The maximum thickness thereof is dependent primarily on mechanical considerations, for example, whether a flexible photoresponsive member is desired.

A very important layer of the photoresponsive device of the present invention is the photoconductive or photogenerating layer comprised of the novel squaraine compositions disclosed herein. These compostions, which are generally electronically compatible with the charge carrier transport layer, enable photoexited charge carriers to travel in both directions across the interface between the photoconductive layer and the charge transport layer.

Generally, the thickness of the photoconductive layer depends on a number of variables including the thicknesses of the other layers, and the percent mixture of the photoconductive material present. Accordingly, this layer can be of a thickness of from about 0.05 microns to about 10 microns when the photoconductive squaraine composition is present in an amount of from about 4 percent to about 100 percent by volume. Preferably this layer is of a width of from about 0.25 microns to about 1 micron when the photoconductive squaraine composition is present in an amount of 30 percent by volume. The maximum thickness of this layer is dependent primarily on mechanical considerations, and whether a flexible photoresponsive device is desired.

The inorganic photogenerating compounds, or the photoconductive materials can comprise 100 percent of the respective layers; or they can be dispersed in various suitable inorganic or resinous polymer binder materials in amounts of from about 5 percent by volume to about 95 percent by volume, and preferably in amounts of from about 25 percent by volume to about 75 percent by volume. Illustrative examples of polymeric binder resinous materials that can be selected include those as disclosed, for example, in U.S. Pat. No. 3,121,006, the disclosure of which is totally incorporated herein by reference; polyesters, polyvinyl butyral, Formvar®, polycarbonate resins, polyvinyl carbazole, epoxy resins, phenoxy resins, especially the commercially available poly(hydroxyether) resins, and the like.

In one embodiment of the present invention, the charge carrier transport material, such as the diamine described hereinafter, may be incorporated into the photogenerating layer, or into the photoconductive layer in amounts, for example, of from about zero volume percent to 60 volume percent. The charge carrier transport layers, such as layer 14, which are of a thickness in the range of from about 5 microns to about 50 microns, and preferably from about 20 microns to about 40 microns, can be comprised of a number of suitable materials which are capable of transporting holes. In a preferred embodiment the transport layer comprises molecules of the formula:

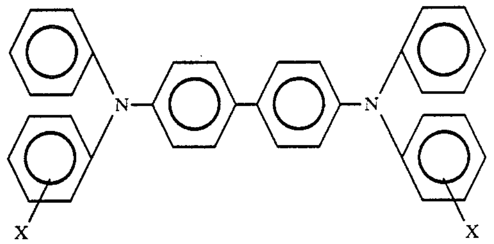

dispersed in a highly insulating and transparent organic resinous binder wherein X is selected from the group consisting of alkyl, and halogen, especially (ortho) $CH_3$, (meta) $CH_3$, (para) $CH_3$, (ortho) Cl, (meta) Cl, and (para) Cl.

Compounds corresponding to the above formula include, for example, N,N-diphenyl-N,N''-bis(alkylphenyl)-[1,1-biphenyl]-4,4'-diamines wherein alkyl is selected from the group consisting of methyl, such as 2-methyl, 3-methyl and 4-methyl, ethyl, propyl, butyl, hexyl and the like. With halo substitution, the amine is N,N'-diphenyl-N,N'-bis(halophenyl)-[1,1-biphenyl]-4,4'-diamine wherein halo is 2-chloro, 3-chloro or 4-chloro.

Providing the objectives of the present invention are achieved, other charge carrier transport molecules can be selected for the photoconductive imaging member of the present invention.

Examples of the highly insulating and transparent resinous binders for the transport molecules include the substances as described in U.S. Pat. No. 3,121,006, the disclosure of which is totally incorporated herein by reference. Specific examples of organic binders are polycarbonates, acrylate polymers, vinyl polymers, cellulose polymers, polyesters, polysiloxanes, polyamides, polyurethanes and epoxies as well as block, random or alternating copolymers thereof. Preferred electrically inactive binder materials are polycarbonate resins having a molecular weight (Mw) of from about 20,000 to about 100,000 with a molecular weight in the range of from about 50,000 to about 100,000 being particularly preferred. Generally, the resinous binder has present therein from about 10 to about 75 percent by weight, and preferably from about 35 percent to about 50 percent, of the active material corresponding to the foregoing formula.

Also included within the scope of the present invention are methods of imaging with the photoresponsive imaging member illustrated herein. These methods are initiated with the formation of an electrostatic latent image on the member from a white light source, followed by development, transfer, and fixing. In printing processes, the exposure step is accomplished with a laser device, or image bar rather than a broad spectrum white light source; and an infrared sensitive imaging member is selected.

The invention will now be described in detail with reference to specific preferred embodiments thereof, it being understood that these examples are intended to be illustrative only. The invention is not intended to be limited to the materials, conditions, or process parameters recited herein; and all parts and percentages are by weight unless otherwise indicated.

EXAMPLE I

There was prepared the fluorinated squaraine bis(4-dimethylamino-2-fluoro-6-methylphenyl) squaraine by suspending 1.14 grams, 10 millimoles, of squaric acid, in 100 milliliters of dry 1-heptanol; and thereafter there was added to the resulting mixture 3.67 grams, 24 millimoles of N,N- dimethyl-3-fluoro-5-methylaniline. This mixture was then sealed in a flask, and the vacuum adjusted so as to enable refluxing at 71° to 75° C. upon heating causing a conversion from a clear color to yellow, and finally to a green color. After about 3.5 hours crystals were observed. The reaction was then allowed to continue for 22.5 hours, at which time refluxing was discontinued, followed by cooling to room temperature. Subsequently, there was separated by filtration 650 milligrams, 17 percent yield, a green crystalline product of the above squaraine. Proton NMR ($CDCl_3$): 2.758 (s, 6H, 6-$CH_3$ ), 3.154 (s, 12H, $NCH_3$), 6.197 (d of d, $^3J_{HF}$=13.7 $H_2$, $^4J_{HH}$=2.56 $H_2$, 2H, H-3), 6.398 (d, $^3J_{HH}$=2.56 $H_2$, 2H, H-5).

EXAMPLE II

The reactant 1-dimethylamino-3-fluoro-5-methylbenzene was prepared by mixing in a 250 milliliter round-bottomed flask, 12.7 grams, 0.102 mol, of 3-fluoro-5-methyl aniline, and 11.5 grams, 0.081 mol of trimethyl phosphate. Thereafter, the reaction mixture was heated at 170° C. for four hours. Subsequent to cooling, 9.97 grams of a solution of sodium hydroxide in 42 milliliters of water, followed by another 50 milliliters of water, was added to the flask. The aqueous workup mixture was then extracted with five 30 milliliter portions of diethyl ether. On evaporation of the diethyl ether solvent, there resulted 9 grams of a syrup product. Distillation at 12 Torr yielded a colorless liquid, 7.5 grams, 48 percent yield of 1-dimethylamino-3-fluoro-5-methyl benzene.

Proton NMR ($CDCl_3$): 2.887 (s,6H, $NCH_3$), 2.269 (s, 3H, $ArCH_3$), 6.1-6.3 (m, 3H, aromatic protons).

Carbon NMR ($CDCl_3$): 21.793 ($^4J_{CF}$=2.3 Hz), 40.115, 96.721 ($^2J_{CF}$=26.0), 103.901 ($^2J_{CF}$=21.8 Hz), 108.796 ($^4$JCF=1.8 Hz), 140.280 ($^3J_{CF}$=10.1 Hz), 152.175 ($^3J_{CF}$=11.3 Hz), 164.316 ($^1J_{CF}$=240.7 Hz).

EXAMPLE III

A photoresponsive imaging member was prepared by providing an aluminized Mylar substrate in a thickness of 75 microns, followed by applying thereto with a multiple clearance film applicator, in a wet thickness of 12.5 microns, a layer of N-methyl-3-aminopropyltrimethoxysilane, available from PCR Research Chemicals, Florida, in ethanol, in a 1:20 volume ratio. This layer was then allowed to dry for 5 minutes at room temperature, followed by curing for 10 minutes at 110° C. in a forced air oven.

There was then applied to the silane layer 0.5 percent by weight of an adhesive available from DuPont Chemical as 49,000 polyester in methylene chloride and 1,1,2-trichloroethane (4:1 volume ratio), with a multiple clearance film applicator to a wet thickness of 12.5 microns. The layer was allowed to dry for one minute at room temperature and 10 minutes at 100° C. in a forced air oven. The resulting layer had a dry thickness of 0.05 microns.

A photogenerating layer was then prepared in the following manner: In separate 2 oz. amber bottles there were added 0.15 gram of the fluorinated squaraine prepared in accordance with Example I, 0.35 gram of Vitel PE-100®, a polyester available from Goodyear, 70 grams of ⅛ inch stainless steel shot, and 9.5 grams of tetrahydrofuran. The above mixture was placed on a ball mill for 24 hours, and the resulting slurry was coated on the polyester adhesive with a multiple clearance film applicator to a wet thickness of 25 microns. The photogenerating layer was then allowed to air dry for 5 minutes, and the resulting member was then dried at 135° C. for 6 minutes in a forced air oven. The dry thickness of the photogenerating layer was 0.9 micron.

There was then prepared a transport layer by the mixing of 65 percent by weight Merlon®, 39 polycarbonate resin with 35 percent by weight N,N'-diphenyl-N,N'-bis(3-methylphenyl)-1,1'-biphenyl-4,4'-diamine. This solution was then mixed to 9 percent by weight in methylene chloride. All of these components were then placed in an amber bottle and dissolved. The resulting mixture was coated with a multiple clearance film applicator (200 microns wet gap thickness) to give a layer with a dry thickness of 16 microns on top of the above fluorinated squaraine photogenerating layer. The resulting imaging member was then air dried at room temperature for 20 minutes, followed by drying in a forced air oven at 135° C. for 6 minutes.

EXAMPLE IV

A photoresponsive imaging member was prepared by repeating the procedure of Example I with the exception that there was selected for preparation of the photogenerating layer 9.5 grams of methylene chloride in place of the 9.5 grams of tetrahydrofuran.

EXAMPLE V

A photoresponsive imaging member was prepared by repeating the procedure of Example III with the exception that there was selected for the preparation of the photogenerating layer 0.35 gram of the phenoxy resin PKHH, available from Union Carbide, in place of 0.35 gram of the polyester resin.

The imaging members as prepared in the above Examples were then tested for photosensitivity in the visible and infrared region of the spectrum by negatively charging with corona to −800 volts, followed by simultaneously exposing each member to monochromic light in the wavelength region of about 400 to about 1,000 nanometers. The photoresponsive imaging members of Examples III, IV or V responded to light in the wavelength region of 400 to 950 nanometers, indicating both visible and infrared photosensitivity.

Also, the surface potential of each of the imaging members of Example III was measured with an electrical probe after exposure to the given wavelengths, and the percent discharge indicating photoresponsiveness, was calculated. Additionally, the imaging members as prepared in Example III were tested for photosensitivity by charging in the dark to a surface potential of −800 volts, followed by measuring with an electrical probe the amount of light energy of monochromatic light supplied by a Xenon lamp in ergs/cm$^2$ required to discharge the member to ½ of its surface potential. Percent discharges and $E_{1/2}$ were then recorded. More specifically, the percent discharge values for exposure to 10 ergs/cm$^2$ of 830, and 400 to 700 nanometers illumination were 66 percent and 52 percent, respectively. These values indicate excellent infrared and visible photosensitivity.

The imaging member of Example III was characterized by an $E_{\frac{1}{2}}$ value of 5.5 and 9.5 ergs/cm$^2$ at 830, and 400 to 700 nanometers, respectively, while exhibiting a dark decay of 57 volts per second. Low values of $E_{\frac{1}{2}}$, that is for example below 100, indicate excellent photosensitivity. In contrast, an identical imaging member with the exception that the photogenerating pigment is bis(4-dimethylamino-2-fluorophenyl) squaraine exhibited excess dark decay, that is, greater than 200 volts per second. Also, this imaging member had an $E_{\frac{1}{2}}$ of 2.5.

These results indicate that a photoresponsive imaging member of Example III would exhibit good copy quality, substantially no background deposits, when incorporated into a xerographic imaging test fixture.

Although the invention has been described with reference to specific preferred embodiments, it is not intended to be limited thereto, rather those skilled in the art will recognize variations and modifications may be made therein which are within the spirit of the present invention and within the scope of the following claims.

What is claimed is:

1. Symmetrical fluorinated squaraine compounds of the following formula:

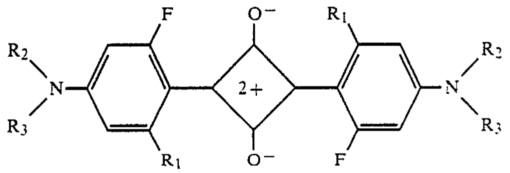

wherein $R_1$, $R_2$ and $R_3$ are selected from the group consisting of alkyl, aryl, and heterocyclic substituents, subject to the provision that each $R_1$, $R_2$ and $R_3$ represent identical substituents.

2. A fluorinated squaraine compound in accordance with claim 1 wherein the alkyl substituents are from 1 carbon atom to about 20 carbon atoms.

3. A fluorinated squaraine compound in accordance with claim 1 wherein the alkyl substituents are from 1 carbon atom to about 6 carbon atoms.

4. A fluorinated squaraine compound in accordance with claim 1 wherein the alkyl substituents are methyl.

5. A fluorinated squaraine compound in accordance with claim 1 wherein the aryl substituents contain from 6 to about 24 carbon atoms.

6. A fluorinated squaraine compound in accordance with claim 5 wherein the aryl substituent is phenyl.

7. The squaraine composition bis(4-dimethylamine-2-fluoro-6-methylphenyl) squaraine.

* * * * *